United States Patent
Corcos et al.

(10) Patent No.: US 8,872,112 B2
(45) Date of Patent: Oct. 28, 2014

(54) HYBRID THZ IMAGING DETECTOR WITH VERTICAL ANTENNA AND SUB-PIXEL SUSPENDED MEMS THERMAL SENSOR AND ACTUATOR

(75) Inventors: Dan Corcos, Haifa (IL); Michel Despont, Au (CH); Danny Elad, Moshav Liman (IL); Lukas Kull, Zurich (CH); Thomas Morf, Gross (CH); Benny Sheinman, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 483 days.

(21) Appl. No.: 13/251,255

(22) Filed: Oct. 2, 2011

(65) Prior Publication Data

US 2013/0082345 A1 Apr. 4, 2013

(51) Int. Cl.
*G01J 5/02* (2006.01)
*G01N 21/35* (2014.01)
*B81B 3/00* (2006.01)
*H01L 31/09* (2006.01)
*G01J 5/08* (2006.01)
*G01J 5/00* (2006.01)
*G01J 3/42* (2006.01)

(52) U.S. Cl.
CPC .......... *G01N 21/3581* (2013.01); *B81B 3/0081* (2013.01); *G01J 2005/0077* (2013.01); *G01J 3/42* (2013.01); *H01L 31/09* (2013.01); *G01J 5/0837* (2013.01)
USPC ........................................................ 250/341.1

(58) Field of Classification Search
USPC ........................................................ 250/341.1
See application file for complete search history.

(56) References Cited

U.S. PATENT DOCUMENTS

| | | | |
|---|---|---|---|
| 6,441,368 B1 * | 8/2002 | Grinberg et al. | 250/239 |
| 2006/0076493 A1 * | 4/2006 | Bluzer | 250/338.1 |
| 2007/0278407 A1 | 12/2007 | Wood et al. | |
| 2009/0015491 A1 * | 1/2009 | Ikeda et al. | 343/703 |
| 2009/0114822 A1 | 5/2009 | Cox et al. | |
| 2011/0062329 A1 | 3/2011 | Ben-Bassat | |

FOREIGN PATENT DOCUMENTS

WO 2011048170 4/2011

* cited by examiner

*Primary Examiner* — David Porta
*Assistant Examiner* — Mindy Vu (57) ABSTRACT

A THz radiation detector comprising a vertical antenna separated from a suspended platform by an isolating thermal air gap for concentrating THz radiation energy into a smaller suspended MEMS platform upon which a thermal sensor element is located. THz photon energy is converted into electrical energy via a thermally isolated air gap between plates of a coupling capacitor that couples energy from the antenna to the thermal sensor. The capacitor plates used for capacitive coupling of the received signal realize an electro-static actuator whereby the application of a DC bias varies the coupling capacitor gap. The DC bias causes the actuator to pull the suspended platform close to the antenna to reduce the capacitive gap, increasing the coupling capacitance, to touch the antenna array thus quickly discharging the heat induced in the sensor platform or to perform advanced readout operations, such as amplitude modulation and correlated double sampling.

22 Claims, 6 Drawing Sheets

HYBRID THZ IMAGING DETECTOR WITH VERTICAL ANTENNA AND SUB-PIXEL SUSPENDED MEMS THERMAL SENSOR AND ACTUATOR

FIELD OF THE INVENTION

The present invention relates to the field of semiconductor imaging devices, and more particularly relates to a hybrid focal plane array (FPA) THz detector with a vertical antenna and sub-pixel suspended Microelectromechanical Systems (MEMS) based thermal sensor and actuator.

SUMMARY OF THE INVENTION

A THz radiation detector comprising a plurality of antenna arms separated from a suspended platform by an isolating thermal air gap. The detector functions to concentrate THz radiation energy into the smaller suspended MEMS platform (e.g., membrane) upon which a thermal sensor element is located. The THz photon energy is converted into electrical energy by means of a pixilated antenna using capacitive coupling in order to couple this focused energy across the thermally isolated air gap and onto the suspended membrane on which the thermal sensor is located.

The detector mechanism achieves a much stronger, focused THz induced thermal heating of the suspended membrane such that this thermal signal becomes much stronger than the detector temperature noise, even when the detector operates at room temperature. This much higher thermal signal to thermal noise is then converted into a much higher electrical signal to electrical noise by the thermal sensor element.

In addition, the detector mechanism incorporates electrostatic actuation to adjust the length of the gap forming the coupling capacitor. By adjusting the DC bias applied to the capacitive plates, the suspended platform can be made to touch the antenna array thus quickly discharging the heat induced in the sensor platform. The mechanism enables an antenna, whose design and materials are optimized for the THz range, to be coupled to a thermal sensor offering very high sensitivity, while allowing for adjustment of the coupling distance. The tuning possibilities provided by the electro-static actuation allow additional optimization, as well as implementation of efficient readout techniques, such as correlated double sampling (CDS) and signal modulation (AM).

There is thus provided in accordance with the invention, a terahertz (THz) detector assembly, comprising a first dielectric substrate, an antenna array fabricated on said first substrate, said antenna array including a first capacitive plate portion, a second dielectric substrate, a sensor array constructed on said second dielectric substrate, said sensor array comprising a suspended platform including a second capacitive plate portion and a thermal sensor, said sensor array operative to transfer THz energy received by said antenna array to an electrical load via capacitive coupling and to convert the heat generated by said load to an electrical signal, wherein said capacitive coupling provides thermal isolation between said antenna array and said sensor array, and wherein said assembly is implemented by vertically joining said antenna array to said sensor array so as to establish one or more coupling capacitors made up of the capacitive plate portion of said antenna array and the capacitive plate portion of said sensor array.

There is also provided in accordance with the invention, a terahertz (THz) detector assembly, comprising a first dielectric substrate, an antenna array fabricated on said first substrate, said antenna array including a first capacitive plate, a second dielectric substrate, a sensor array constructed on said second dielectric substrate, said sensor array comprising a suspended platform including a second capacitive plate, a thermal sensor and an electrical load coupled to said second capacitive plate, said suspended platform suspended by one or more holding arms connected to said second dielectric substrate which act as springs allowing said suspended platform to move, wherein a coupling capacitor is formed by vertically joining said antenna array to said sensor array such that said first capacitive plate and said second capacitance plate are separated by a gap, and wherein said sensor array is operative to transfer THz energy received by said antenna array to said electrical load via said coupling capacitor and to convert the heat generated by said electrical load to an electrical signal, wherein said capacitive coupling provides thermal isolation between said antenna array and said sensor array.

There is further provided in accordance with the invention, a terahertz (THz) detector assembly, the method comprising a first dielectric substrate, an antenna fabricated on said first substrate, said antenna including a first capacitive plate, a second dielectric substrate, a suspended platform constructed from said second dielectric substrate and connected thereto via one or more holding arms which act as springs allowing said suspended platform to move, said suspended platform comprising a second capacitive plate, an electrical load and a thermal sensor, wherein a coupling capacitor and associated gap are formed by vertically joining said antenna to said suspended platform sensor array, said coupling capacitor operative to transfer energy received by said antenna to said electrical load, said thermal sensor operative to convert the heat generated by said electrical load to an electrical signal, wherein said coupling capacitor also functions as an electrostatic actuator upon application of a DC bias applied across it which generates an attractive force to move said suspended platform in the vertical direction, whereby the final position of said suspended platform is determined by a balance between the electro-static force and an opposite mechanical force exerted by said springs.

BRIEF DESCRIPTION OF THE DRAWINGS

The invention is herein described, by way of example only, with reference to the accompanying drawings, wherein.

DETAILED DESCRIPTION OF THE INVENTION

THz radiation imaging is currently a fast developing research area with inherent applications such as THz security imaging which can reveal weapons hidden behind clothing from distances of ten meters or more; or medical THz imaging which can reveal, for example, skin cancer tumors hidden behind the skin and perform fully safe dental imaging. Constructing prior art THz detectors is typically a challenging endeavor since both radiation sources and radiation detectors are complex, difficult and expensive to make.

THz radiation is non-ionizing and is therefore fully safe to humans unlike X-ray radiation. THz imaging for security applications, for example, uses passive imaging technology, namely the capabilities of remote THz imaging without using any THz radiation source thus relying solely on the very low power natural THz radiation which is normally emitted from any room temperature body according to well-known black body radiation physics. Passive THz imaging requires extremely sensitive sensors for remote imaging of this very low power radiation. Prior art passive THz imaging utilizes a hybrid technology of superconductor single detectors cooled to a temperature of about 4 degrees Kelvin which leads to extremely complex (e.g., only the tuning of the temperature takes more than 12 hours before any imaging can take place) and expensive (e.g., $100,000 or more) systems. A detector is desirable that can be used to detect THz radiation and that has much lower potential cost compared with existing superconducting solutions. Passive THz imaging, however, requires three orders of magnitude higher sensitivity compared with passive infrared (IR) imaging, which is a challenging gap.

In addition, the need to cool the detector to cryogenic temperatures for reducing noise in prior art detectors is significant drawback for an imager, which would find its natural field of application in surveillance and inspection activities. Such a cooling apparatus would raise the cost of the system considerably and would make power consumption much larger, limiting its mobility. An active THz system can operate with less sensitive pixels since it relies on reflections of the radiation emitted by a source, embedded in the system; the radiation provided by the source is typically larger than that spontaneously emitted by the target.

Further, processing the signal obtained from active imaging can be complicated because of the possible reflections, interfering with the original light distribution. Passive imaging has the further advantages of allowing covert monitoring and of eliminating any reason of health-related concerns of the public. Solutions offering imaging capabilities at lower frequencies suffer from a limited spatial resolution and scarce compactness. The low-cost aspect is also emphasized since the many potential applications for THz cameras, combined with their availability, would make them a potential object of large scale commercialization.

THz antennas with capacitive coupling provide a challenge to the designer for achieving both high sensitivity (for enabling passive imaging) and fast response time (allowing video frame rates). The efficiency with which the signal is transferred to the thermal sensor strongly depends on the capacitor size. A large parallel plate capacitor is obtained when the plates have a large area and when the gap between them is small. Due to sensitivity requirements, the thermal resistance $R_{th}$ of the thermal sensor must be large (we want $\Delta T_{ss} = P_{opt} \cdot R_{th}$ to be large); but at the same time we need the time constant $\tau = R_{th} C_{th}$ to be small. A small thermal capacitance is obtained when the mass and specific heat of the sensor are small. Hence we can only increase the capacitor area at the expense of the pixel's response time. On the other hand we are limited in scaling the gap size due to the deformation of the suspended structure that follows MEMS post-processing due to the release of residual stress and causes large tolerances; in addition tilting and deformation reduce the nominal capacitance to even smaller values.

The detector consists of a hybrid focal plane array (FPA) for uncooled passive THz imaging that is obtained, in one embodiment, with the use of a CMOS-SOI chip, etched using MEMS processes, and an array of THz antennas electrically coupled to the thermal sensors on the chip. The CMOS-SOI process layers are used both for making the devices (e.g., transistors or diodes working as thermal sensors) and the masks for the subsequent post-processing. The thermal sensors are made of silicon dioxide platforms, suspended by one or more holding arms, after being thermally isolated with a MEMS process. The platform can be electro-statically actuated for implementing tuning and other readout-related operations.

Figure 1:
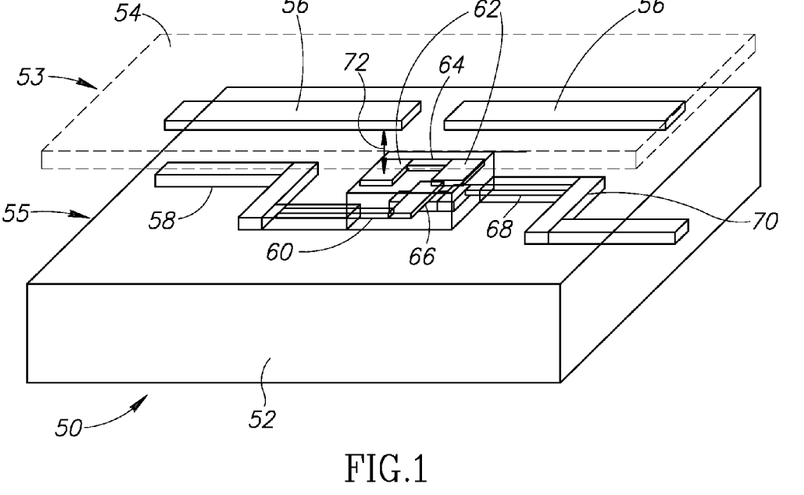
FIG. 1 is a diagram illustrating an example embodiment of a passive THz radiation detector incorporating vertical antenna coupling to the sensor platform.

A diagram illustrating an example embodiment of a passive THz radiation detector incorporating vertical antenna coupling to the sensor platform is shown in FIG. 1. The detector, generally referenced 50, comprises a vertical antenna array 53 aligned over a suspended platform 55. The vertical antenna array 53 comprises a dielectric substrate 54 and antennas 56. The dielectric substrate is preferably transparent to THz radiation. The sensor platform 55 comprises a dielectric substrate 52, holding arms 58, 70, wires 60, 68, capacitive plates 62, electrical load resistor 64 and thermal transistor 66.

Figure 2:
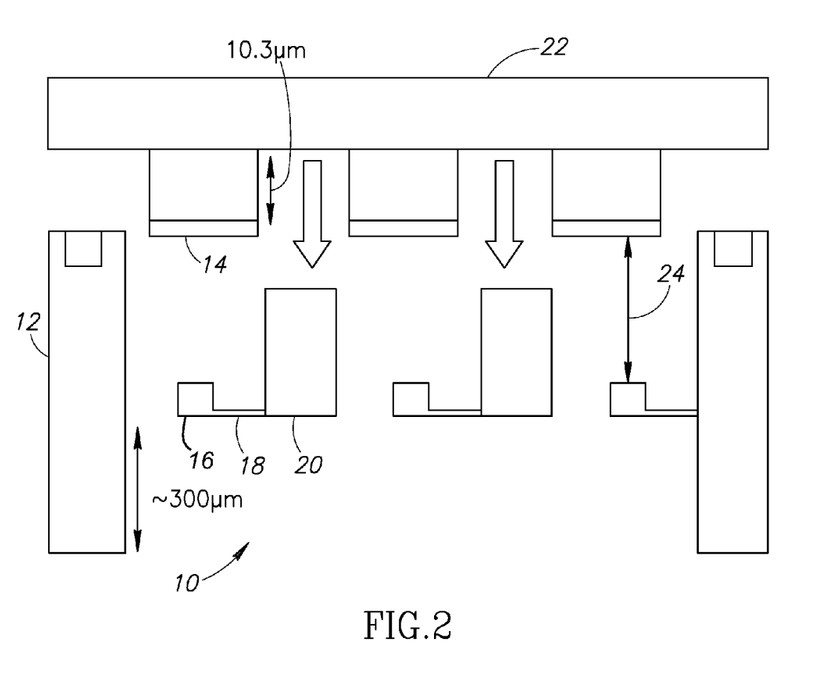
FIG. 2 is a diagram illustrating a side view of the detector assembly before the antenna is vertically joined to the sensor platform.

A diagram illustrating a side view of the detector assembly before the antenna is vertically joined to the sensor platform is shown in FIG. 2. The detector, generally referenced 10, comprises a first dielectric substrate 22 on which an antenna array structure 14 is firmed. A sensor array structure is formed on a second dielectric substrate 12. The sensor array comprises a frame 20, one or more holding arms 18 and a suspended platform 16. The suspended platform comprises capacitive plates, electrical load, thermal sensor (transistor) and RF choke.

The detector assembly is formed by joining the two components, namely the antenna array and sensor array wherein a gap 24 is formed between the two components. The antenna array is placed vertically over the sensor array such that the capacitive plates on the antenna array align with the capacitive plates on the sensor array. Note that in one embodiment, the detector assembly is packaged under vacuum in order to improve the thermal isolation of the sensors.

Figure 7:
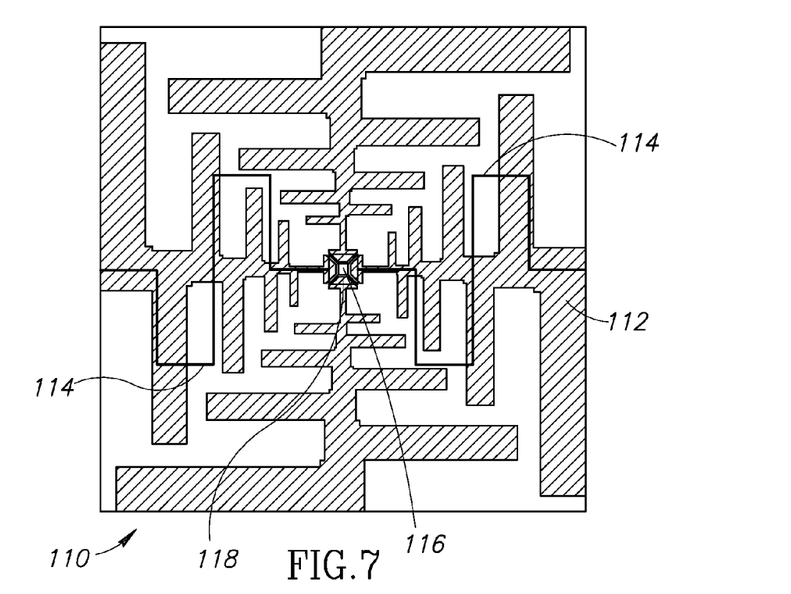
FIG. 7 is a diagram illustrating a top plan view of a pixel after the detector is assembled.

In one embodiment, the antennas are constructed of a metallic material 14 deposited on a dielectric substrate 22, transparent to the desired wavelengths. The specific antenna design can be chosen according to the particular frequency and bandwidth requirements, and is not constrained by the adoption of the solution described in this invention. For example, a log-toothed antenna for the 0.5-1.5 THz range is shown in FIG. 7.

Other possible antenna types include spiral antennas, toothed antennas and slotted antennas. Although it is not critical which antenna type is used, it is preferred that the energy from the antenna is not directly coupled to the detector but rather is capacitive coupled to permit thermal isolation of the thermal sensor element.

The thermal sensors are constructed of devices whose electrical current is strongly dependent upon their temperature. When the radiation detected by the antenna is transferred to the platform hosting the device in the form of an induced current, the sensor heats up and detects the signal. In order to couple between the antenna and the load located on the platform, a plurality of capacitors is used (e.g., four).

Figure 3:
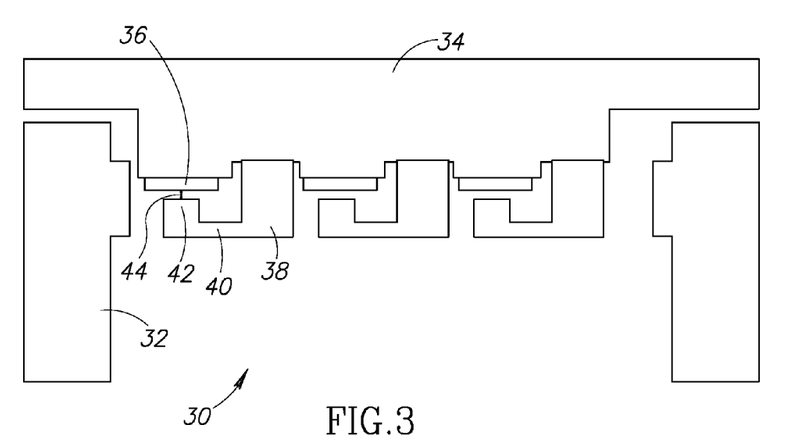
FIG. 3 is a diagram illustrating a side view of the detector assembly after the antenna is vertically joined to the sensor platform.

A diagram illustrating a side view of the detector assembly after the antenna is vertically joined to the sensor platform is shown in FIG. 3. The detector, generally referenced 30, comprises a first dielectric substrate 34 on which an antenna array structure 36 is firmed. A sensor array structure is formed on a second dielectric substrate 32 (CMOS substrate). The sensor array comprises a frame 38, one or more holding arms 40 and a suspended platform 42. The suspended platform comprises capacitive plates, electrical load, thermal sensor (transistor) and RF choke.

The detector assembly is formed by vertically joining the antenna array and sensor array wherein a gap 44 is formed between the two components. The gap is formed between a portion of the antenna that functions as capacitive plates and the capacitive plates in the sensor array to form a coupling capacitor. The antenna array is placed vertically over the sensor array such that the capacitive plates on the antenna array align with the capacitive plates on the sensor array leaving a suitable gap distance 44.

Figure 4:
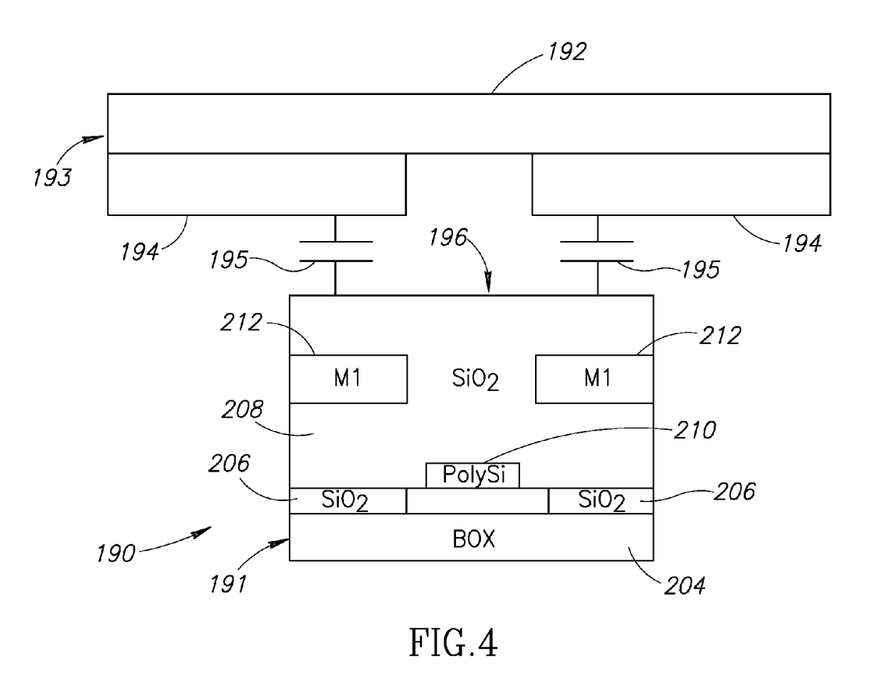
FIG. 4 is a diagram illustrating a cross sectional view of the vertical antenna and sensor platform.

A diagram illustrating a cross sectional view of the vertical antenna and sensor platform is shown in FIG. 4. The detector, generally referenced 190, comprises a vertical antenna array 193 and a sensor platform 191. The antenna array 193 comprises a substrate 192 and antenna 194. The sensor platform 191 comprises a suspended platform 196 that includes BOX layer 204, silicon dioxide layers 206, polysilicon portion 210 (thermal sensor), metal portion M1 212 (capacitive plates) and silicon dioxide 208. Note that capacitors 195 are formed in the gap between the antennas 194 and M1 capacitive plate portions 212.

The THz detector utilizes an electromagnetic coupling technique whereby the optical energy (i.e. THz energy) is first absorbed by the antenna which functions to convert it to electrical energy that is then capacitively coupled to the thermally isolated, released thermal sensor element (e.g., a diode, transistor, etc.). Capacitively coupling the antenna to the thermal sensor element provides thermal isolation of the sensor from the antenna.

Figure 10:
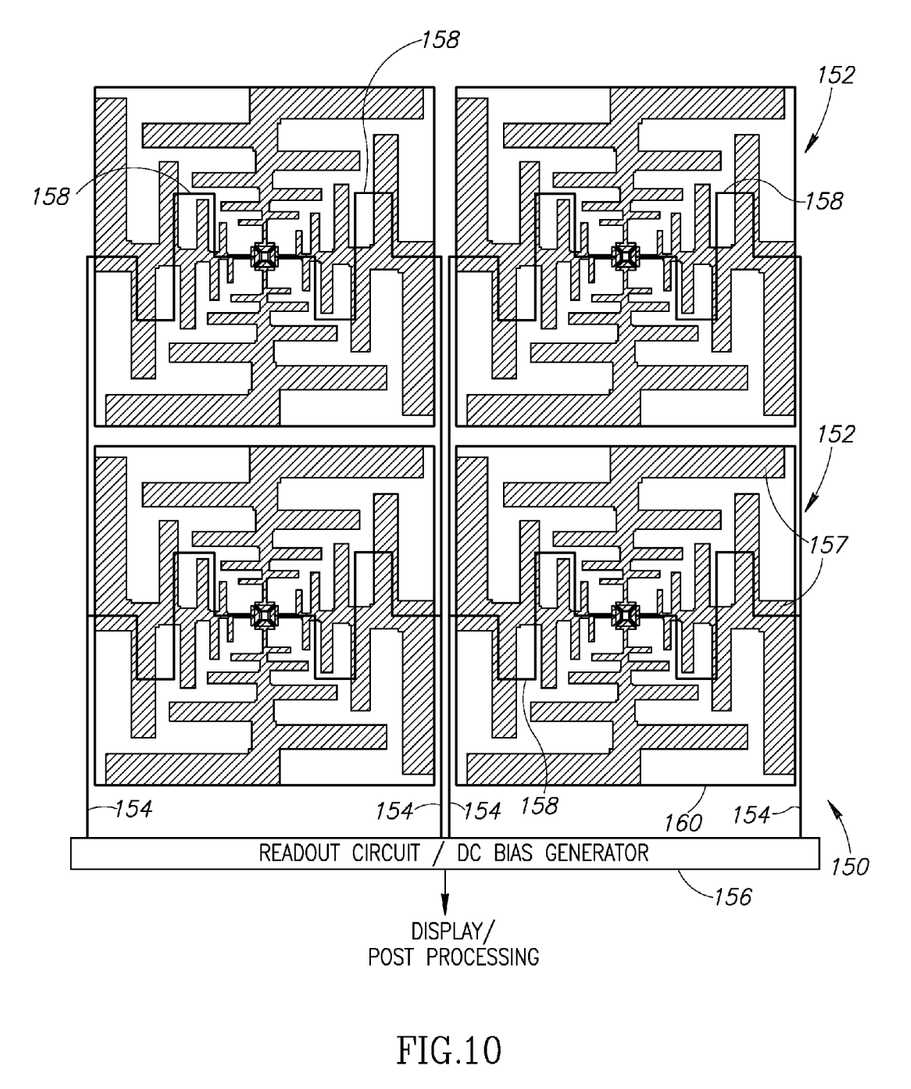
FIG. 10 is a diagram illustrating an example 2×2 pixel matrix using the THz radiation detector of FIG. 7.

In one example embodiment, a plurality of detectors are arranged to receive THz radiation energy in a 2D array configuration, as shown in FIG. 10. In this case, THz radiation energy received in each pixel of the 2D imaging array, whose size, in one example embodiment, is on the order of several hundred microns (e.g., 300 microns square) and concentrated at each pixel at a frequency on the order of 1 THz into a much smaller suspended MEMS platform (of the order of tens microns) on which the THz detector is situated (so that the complete suspended thermally isolated MEMS structure has minimal thermal mass and thermal conductivity). As mentioned hereinabove, this is achieved by means of converting the THz photon energy into electrical energy using a pixilated antenna and by using capacitive coupling to couple this focused antenna energy across the thermally isolated air gap and into the suspended platform on which the thermal sensor is located. This method achieves focused THz induced thermal heating of the suspended platform so that this THz induced thermal signal becomes much stronger than the detector temperature noise, even when the detector operates at room temperature. This higher thermal signal to thermal noise is then converted into a signal having a larger electrical signal to noise ratio by the sensing active device (e.g., transistor). In other words, a thermal conductance discontinuity (e.g., capacitance coupling gap) is created between the antenna and the relatively small suspended platform by means of the MEMS process.

The technique of using capacitive coupling to focus the antenna energy onto an isolated sub-pixel floating platform can be used with a variety of on-chip pixilated antennas, such as the antenna shown in FIG. 7. Focusing the THz energy via the antenna aids in filtering out competing received infrared radiation, since the infrared radiation not being received by the antenna is absorbed by the small suspended platform whose size is substantially smaller than the pixel size. Note that the capacitive coupling can be increased by combining several silicon process back end of line (BEOL) metal levels to form the capacitors and by using interdigitized (i.e. comb like) structures to increase the capacitor area.

In addition, the detector provides impedance matching between the pixilated antenna and the thermal sensor across the coupling capacitance. An antenna with reactive impedance is preferably used that cancels the coupling capacitance at the bandwidth of interest. This can be achieved, for example, by using a bow-tie dipole antenna whose length is larger than half a wavelength and is also possible by an appropriate design of the antenna. The higher than half wavelength antenna also provides a high impedance of several hundred ohms which aids in matching the antenna to the thermal sensor element across the given impedance of the coupling capacitor.

The impedance matching between the antenna and the thermal sensor element is achieved by capacitively coupling the signal into a matched resister, preferably made of polysilicon. Note that in one embodiment, a cross shaped resistor made of polysilicon is mated with a standard NMOS transistor located in the vicinity of the resistor. Note that in an alternative embodiment, this approach is modified to permit separating the two different polarizations of the received THz radiation. This can be useful to identify polarized radiation such as obtained from reflection by flat surfaces.

The capacitance coupling between the suspended, thermally isolated, platform and the antenna arms can be significantly increased if the length over which they are made parallel to each other is increased. The same coupling capacitance can be increased by making the parallel spacing between the antenna and the platform smaller. This, however, depends on the quality of the MEMS process being used. A better MEMS process allows this spacing to decrease without the risk of having an electrical short between the antenna and the coupling capacitance metals in the platform.

Figure 5:
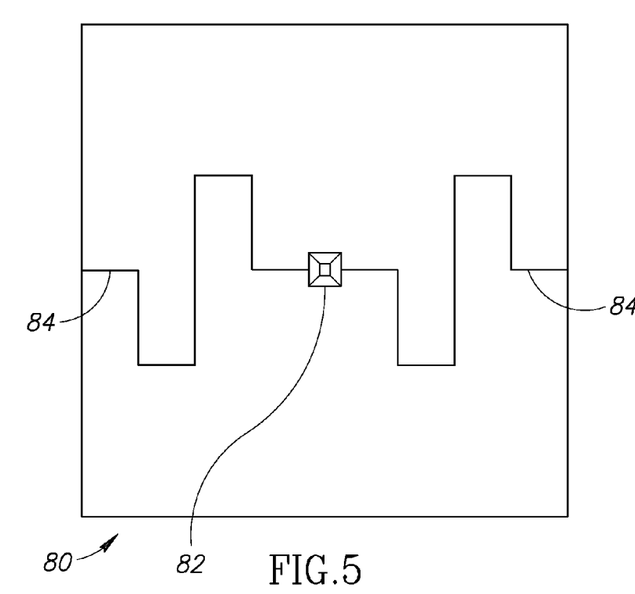
FIG. 5 is a diagram illustrating a top plan view of the suspended platform and holding arms of a pixel before the detector is assembled.

A diagram illustrating a top plan view of the suspended platform and holding arms of a pixel before the detector is assembled is shown in FIG. 5. In one embodiment, the detector, generally referenced 80, comprises a sensor array platform 82 suspended via holding arms 84. The sensor array comprises capacitive plates, electrical load and thermal sensor. Note that the antenna structure is not shown to aid in illustrating the configuration of the holding arms and sensor platform. It is appreciated that a number of holding arms other than two may be used depending on the particular implementation.

Figure 6:
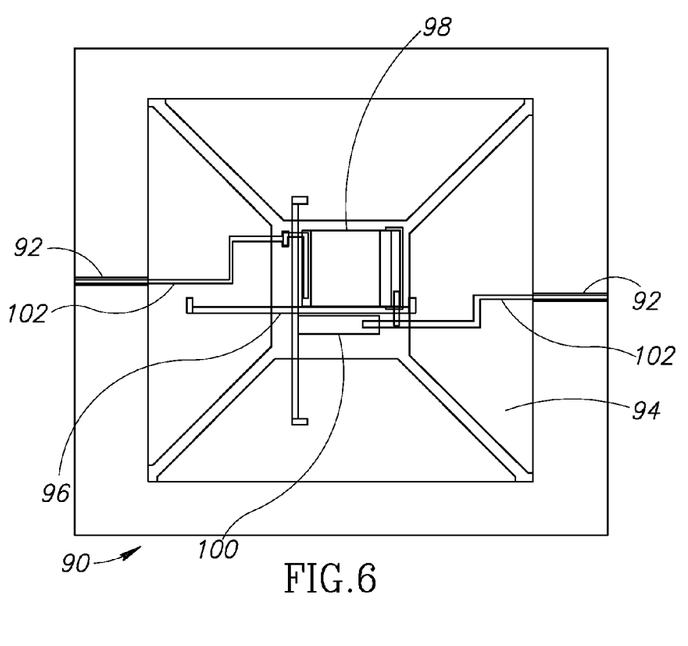
FIG. 6 is a diagram illustrating a top plan view of the suspended platform in more detail before the detector is assembled.

A diagram illustrating a top plan view of the suspended platform in more detail before the detector is assembled is shown in FIG. 6. In one embodiment, the detector, generally referenced 100, comprises a plurality of capacitive plates 94 (e.g., four), holding arms 92, wires 102, electrical load resistor 96, thermal sensor (transistor) 98 and RF choke 100.

Note that the antenna structure is not shown to aid in illustrating the configuration of the holding arms and sensor platform. The electrical load 96 is connected to all four capacitive plates 94. Energy focused by the antenna is capacitive coupled to the electrical load which heats up as a response. The heat is sensed by the thermal sensor 98 and converted to an electrical signal.

A diagram illustrating a top plan view of a pixel after the detector is assembled is shown in FIG. 7. The detector, generally referenced 110, comprises antenna array 112, holding arms 114 sensor platform 118 and coupling capacitors 116.

Figure 8:
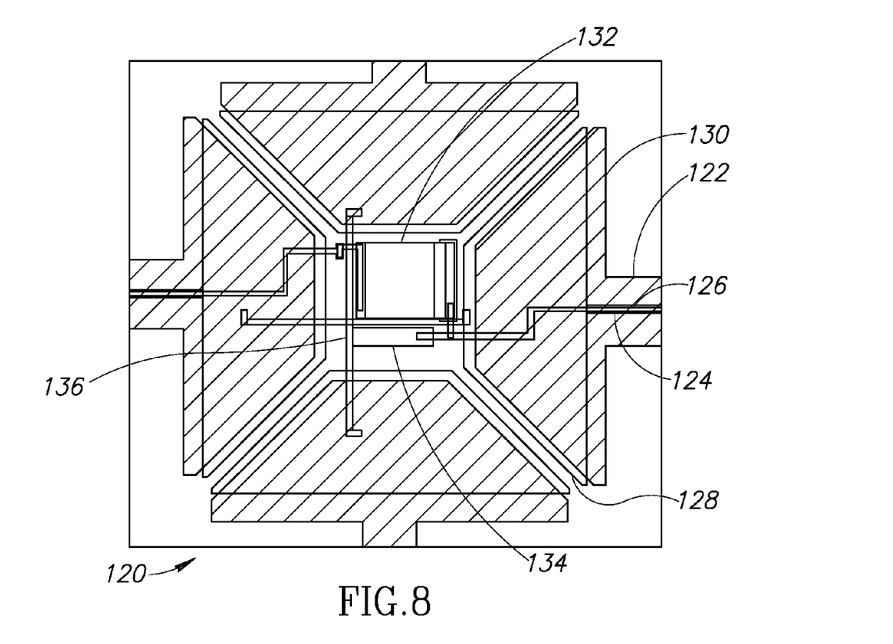
FIG. 8 is a diagram illustrating a top plan view of the suspended platform in more detail before the detector is assembled.

A diagram illustrating a top plan view of the suspended platform in more detail before the detector is assembled is shown in FIG. 8. The detector, generally referenced 120, comprises antenna elements 122, holding arms 124, wires 126, four lower capacitive plates 128 (on sensor suspended platform), four upper capacitive plates 130 (on vertical antenna), electrical load 136, RF choke 134 and thermal sensor 132.

With reference to FIGS. 1 to 8, in one embodiment, since blackbody emission is randomly polarized, a set of two orthogonal antennas can be used to increase the absorption efficiency. Each group of terminals is terminated by a load, whose resistance is matched to the radiation resistance of the antenna. A plurality (e.g., four) of capacitors is formed in the overlap area of the terminal lobes of the four antennas and the first metallization layer (M1) of the underlying platform. The gap between these electrodes is preferably relatively small in order to yield a large capacitance, which in turn is desirable in achieving high coupling efficiency. The electromagnetic energy carried by the THz radiation is thus transferred to the matched polysilicon loads located on the platform.

The same capacitive plates of the coupling capacitors that are used for transferring the optical signal are also used as electrodes of an electro-static actuator. Such a device permits the suspended platform to move along the field's direction of the platform (i.e. the vertical direction). The one or more holding arms supporting the suspended platform act as springs. The elasticity of the springs is determined by the geometry of the long and narrow holding arms supporting the suspended platform. Application of a DC bias to the capacitive plates of the coupling capacitor causes the actuation of the electro-static actuator. The DC bias is preferably applied through an RF choke in order to preserve the AC signal induced by THz radiation. In one embodiment, the RF choke is connected to the middle of the antenna's loads, where the two load resistors cross each other. In one embodiment, the DC bias is set by the voltage applied to the antenna side of the capacitor, while the plates on the platform are kept at ground potential. The ground signal is routed by the same wire that is also connected to the sensing device (i.e. transistor or diode).

The electro-static actuator enables the suspended platform to be adjusted in height relative to the antenna thus permitting adjustment of the gap width of the coupling capacitor, which in turn determines it capacitance.

In a first calibration stage of a two-step scheme of the mechanism, each element (i.e., each pixel) of the array is examined. The desired height of the suspended platform is attained by gradually increasing the DC bias on the capacitor and by measuring the gap (for example with an optical profilometer or with an electrical AC measurement). Each control voltage is sampled, converted with an analog-to-digital converter and stored in memory.

In a second operation stage of the mechanism, the memory location is accessed where calibration data was previously stored. The calibration data is retrieved and reconstructed by a digital-to-analog converter and applied to the coupling capacitors, thereby adjusting their air gap.

Considering an array of detectors, each individual detector can be calibrated in this manner and the DC biases determined during the calibration stage associated with each detector stored for use during the operational stage.

The electro-static actuators fabricated from the coupling capacitors enables several operations to be performed aimed at improving the performance of the THz sensor/detector. In a first operation, the coupling capacitance is tuned through control of the air gap between the suspended platform and antenna array. This is useful in the case of tilting, which is caused by the residual stress following the MEMS post-processing procedures. The antenna array is positioned on top of the dielectric substrate (e.g., the CMOS-SOI chip) where the suspended thermal sensors are fabricated.

The thermal sensors are suspended by holding arms which, due to their length and compliance, act as springs and allow the suspended platforms to move. In particular, when a DC bias is applied between the capacitor plates, the accumulated electrical charges produce an attractive force causing the platforms to move in the vertical direction. Their final position is determined by the balance between the electro-static force and the opposing mechanical force exerted by the spring. Application of an appropriate DC bias, can reduce the initial capacitive gap by almost a third. Considering use of a current drive method, then a stable full range of travel (up to a zero gap size) can be achieved.

In a second operation, fast discharge of the radiation-induced heat on the suspended platform is affected by causing the suspended platform to touch the antenna. This capability enables implementing a correlated double sampling (CDS) algorithm. CDS is a well-known technique for filtering low-frequency flicker (1/f) noise, which is self-correlated. This is achieved by sampling the output of the detector when the optical signal is on thus yielding signal and noise, and sampling and measuring again when the signal is turned off thus measuring only noise. By subtracting the two measurements, assuming they were made in very close instances in time, the 1/f noise can be reduced.

When CDS is applied to thermal sensors, obstructing the optical signal with a shutter is not sufficient. A memory effect is provided by the heat, which will cause the temperature of the thermal sensor to be higher than the sink until a few thermal time constants have elapsed. Thus, in order to "reset" the sensors output signal, a fast cool-down procedure is performed. This is achieved by applying an appropriate DC bias voltage to the electro-static actuator that brings the capacitive plates on the suspended platform to a distance closer than ⅔ of the original gap (known as "pull-in" distance). This causes the suspended platform to collapse onto the antenna, which is a good heat sink, until a point in time when the DC bias voltage is removed.

In a third operation, the electro-optical signal is amplitude modulated through the periodical variation of the coupling gap. In another scheme for attenuating low-frequency noise signals, which are often dominant in thermal sensors, the received signal is modulated and thus moved in the frequency domain to a frequency band where white noise is dominant. Then, in order to read the sensor output, the readout circuit demodulates the signal back to its original frequency. The use of well-known signal modulation and demodulation is typically obtained with a chopper wheel, periodically opening and obstructing the sensor's field of view. A more efficient solution for modulating the signal is to vary the gap of the coupling capacitor with the appropriate DC bias voltage. Due to the high dependence of the coupling efficiency upon the coupling capacitance, and hence the gap size, it is possible to periodically vary this distance and to achieve a modulation in the electro-optical signal, thus eliminating the need for an optical chopper wheel.

Thus, the detector mechanism of the present invention uses electro-static actuation to realize an efficient, high performance THz sensor structure that comprises (1) vertical capacitive coupling between the antenna and thermal sensor, simplifying MEMS post-processing and increasing the capacitance to volume ratio; (2) pulling the suspended platform close to the antenna using electro-static force to reduce the capacitive gap and increase the coupling capacitance, thus improving the coupling efficiency; (3) using the same capacitor plates (that are required for capacitive coupling of the received signal) to realize the electro-static actuator, supplying DC bias through an RF choke; and (4) using the pulling capability to perform advanced readout operations, such as amplitude modulation (AM) and correlated double sampling (CDS).

Figure 9:
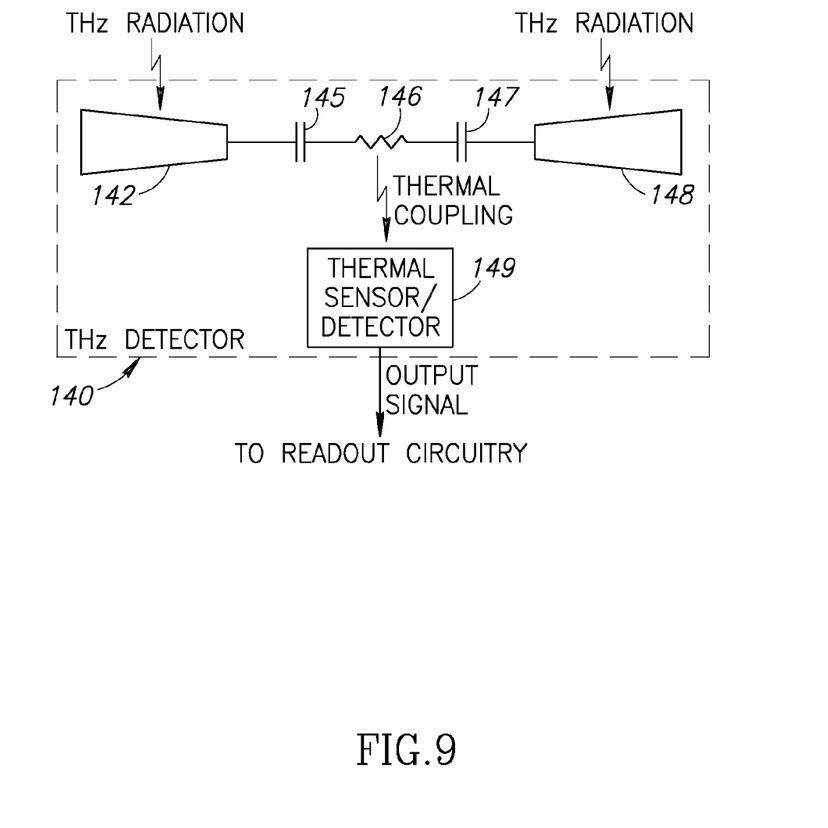
FIG. 9 is a diagram illustrating the electrical and thermal coupling in the detector.

A circuit diagram illustrating an equivalent circuit for the THz radiation detector of FIG. 1 is shown in FIG. 9. The detector, generally referenced 140, comprises a plurality of antennas elements 142, coupling capacitors 145, electrical load (heating element, e.g., resistor) 146 and thermal sensor 149 thermally coupled to resistor 146.

A diagram illustrating an illustrative example of a small 2×2 pixel imaging matrix using the THz radiation detector of FIG. 7 is shown in FIG. 10. Note that using the techniques described herein, one skilled in the art can construct much larger matrices of several hundred pixels to create the required high resolution image. The imaging matrix, generally referenced 150, comprises a plurality of detectors 152 (four in this example embodiment), sensor signal lines 154 and read-out circuitry/DC bias generator 156. Each detector comprises antenna arms 157, suspended platform 160 and holding arms 158. The output of the sensors located on the platforms is input to the read-out circuit 156 for display or further post-processing. Circuit block 156 also functions to generate the DC bias voltages for activating the electro-static actuator to adjust the suspended platform in height. Note that in one embodiment, the pixel array is surrounded by dummy pixel rows and columns. Dummy rows and columns are used to keep the same MEMS and VLSI fabrication conditions for the pixels residing at the periphery of the two dimensional array.

To aid in understanding the operation of the THz detector of the present invention, an example calculation is provided to show quantitatively that room temperature passive THz imaging is a possibility at video rates utilizing the detector.

In this example, a predefined bandwidth of 0.5 to 1.5 THz is assumed, which contains black body power of $I=2.857 \times 10^{-5}$ Watt/cm$^2$ at a temperature of 300 Kelvin. The corresponding black body power temperature sensitivity per degree Kelvin is given as $$dI/dT = 1.043 \times 10^{-7} \text{ Watt/cm}^2/^\circ \text{K} \quad (1)$$

at T=300K when integrating from 0.5 to 1.5 THz. Let us assume that the overall radiation reception efficiency, considering atmospheric losses, lens losses, emissivity of the target less than one, pixel fill factor, efficiency of the antenna and impedance matching losses, etc. is given as $$\eta_{total} = \eta_{env} \times \eta = 0.3 \quad (2)$$

where $\eta$ is the efficiency of the detector;

$\eta_{env}$ is the efficiency of the environment (i.e. anything other than the detector).

Note that the value of 0.3 is reasonable to assume at this stage. Let us assume that the pixel size is $A_D = 200 \times 200$ um$^2$ which is the wavelength at the higher end frequency of 1.5 THz and is therefore the best resolution limit which we can achieve at this frequency. Note that in the lower frequencies several pixels are used together to attain higher sensitivity of the unified larger pixel.

Let us assume a frame time of $\tau = 70$ msec which corresponds to a video frame rate of 14 Hz, sufficient for the human eye. Higher frame rates are possible but they reduce the signal to noise ratio. Let us further assume that we are using a plastic THz lens with an $F_\# = 1$ (i.e. the ratio of the focal length F to the lens diameter D). Alternatively, better optics may be used at the expense of large lens diameters or mirror combinations, etc. For this exemplary calculation, however, we assume simple feasible optics. Let us now assume a noise equivalent temperature difference (NETD) in the target of NETD=0.5° K which is sufficient for high quality thermal imaging.

Assuming the above stated values, the THz signal received by each pixel for a temperature change at the target of $\Delta$=NETD=0.5 Kelvin is Ps=NEP=1.56 picowatt. Note that this is the received power change per target 0.5 degree change, where the total target power received by each pixel, namely the background power, is approximately $8.57 \times 10^{-10}$ Watt. We calculate this using the well-known equation as follows $$Ps = \frac{dI}{dT} \times \Delta T \times A_D \times \frac{1}{4F_\#^2} \eta_{total} \quad (3)$$

where we replace $dI/dT \times \Delta T$ by the power density I for the calculation of the background power.

Let us now make the ideal assumption that the main detector noise is the fundamental thermal fluctuation noise due to the finite heat capacity of the platform. This is adequate for an initial start since the thermal fluctuation noise is always left even after we minimize the added electrical noises from the thermal sensor element itself. Assuming this, we can use the known relation for the Noise Equivalent Power (NEP) of the detector due only to the thermal fluctuation noise and equate it to the above calculated signal for reaching a unity signal to noise ratio as follows $$Ps = NEP \times \eta = \sqrt{\frac{kT^2 G_{th}}{\tau}} \quad (4)$$

Assuming that this same received power can be concentrated using capacitive coupling from the receiving antenna into the thermally isolated suspended platform, we obtain the desired threshold signal to noise of unity when the thermal conductivity of the platform is given by:

$$G_{th} = \frac{Ps^2 \tau}{kT^2} \quad (5)$$

which yields a required holding arm thermal conductivity of $1.243 \times 10^{-7}$ Watt/° K assuming a detector temperature of 315 degrees Kelvin (40 degrees Celsius). Note that better results are obtained when the detector is cooled somewhat and maintained, using a closed cycle system, at a fixed temperature somewhat lower than room temperature.

Using the material properties of an example 0.18 um SOI semiconductor process results in a thermal conductivity that corresponds to a suspended platform of 50 micron×50 micron and which has a thermal heat capacity of Cth=8.70×10$^{-9}$ Joule/Kelvin in the sense that they both provide the desired time constant of 70 milliseconds. Following the same calculation, focusing all the energy on a platform smaller than 50 micron by 50 micron, we obtain better performance than this (i.e. a lower NEP) limited by the ability to design and release a small platform, as well by the physical required size of the thermal sensor element (e.g., sensing transistor) which is located on this platform.

Let us now consider the electrical noise processes of the sensor element (e.g., sensing transistor). The expression for the NEP of the detector while also considering the added electrical noises is $$NEP \times \eta = \sqrt{\frac{kT^2 G_{th}}{\tau} + \frac{2qG_{th}^2 B}{TCC^2 I_D} + \frac{K_f G_{th}^2 \ln(f2/f1)}{TCC^2}} \quad (6)$$

These electrical noises, assuming that the transistor is at subthreshold, include two added terms to the NEP expression which are the fundamental shot noise (in the center) and the technology dependent 1/f noise (on the right). In order to lower the relative effect of shot noise we need a sufficiently large threshold detector current $I_D$, e.g., about several 100 nAs. In order to lower the 1/f noise a larger transistor is used which has a higher TCC for the same bias current, and also has a lower $K_f$. It also follows from Equation 6 that if we further reduce the holding arm thermal conductivity, we obtain a significant reduction in the relative impact of these added electrical noises. We can do so by targeting a much smaller platform than 50 micron×50 micron, which can be (in principle) as low as 10 micron×10 micron, thereby reducing the electrical noises by a factor of 625 and the thermal fluctuation noise by a factor of 25.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. As numerous modifications and changes will readily occur to those skilled in the art, it is intended that the invention not be limited to the limited number of embodiments described herein. Accordingly, it will be appreciated that all suitable variations, modifications and equivalents may be resorted to, falling within the spirit and scope of the present invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A terahertz (THz) detector assembly, comprising:
    a first dielectric substrate;
    an antenna array fabricated on said first substrate, said antenna array including a first capacitive plate portion;
    a second dielectric substrate;
    a sensor array constructed on said second dielectric substrate, said sensor array comprising a suspended platform including a second capacitive plate portion and a thermal sensor, said sensor array operative to transfer THz energy received by said antenna array to an electrical load via capacitive coupling and to convert the heat generated by said load to an electrical signal, wherein said capacitive coupling provides thermal isolation between said antenna array and said sensor array, and wherein said suspended platform is suspended by one or more holding arms connected to said second dielectric substrate, the one or more holding arms acting as springs allowing said suspended platform to move; and
    wherein said assembly is implemented by vertically joining said antenna array to said sensor array so as to establish one or more coupling capacitors made up of the capacitive plate portion of said antenna array and the capacitive plate portion of said sensor array.

2. The detector according to claim 1, wherein a DC bias voltage applied across said one or more capacitors forms an electro-static actuator.

3. The detector according to claim 1, wherein current induced in said electrical load causes said thermal sensor to heat up and detect said THz received signal.

4. The detector according to claim 1, wherein said one or more coupling capacitors are adapted to couple THz energy from said antenna array and also form electrodes of an electro-static actuator which allows the gap of said one or more coupling capacitors to be adjusted in accordance with a DC bias applied to said electrodes.

5. The detector according to claim 1, wherein said one or more coupling capacitors are adapted to couple THz energy from said antenna array and also form electrodes of an electro-static actuator operative to move said suspended platform, acting as a spring, thereby allowing the gap of said one or more coupling capacitors to be adjusted in accordance with a DC potential applied to said electrodes.

6. The detector according to claim 1, wherein said one or more coupling capacitors are adapted to couple THz energy from said antenna array and also form electrodes of an electro-static actuator operative for adjusting said suspended platform to a desired height during a calibration phase where a DC bias level required for each detector in an array is stored and later retrieved during an operation phase where it is applied to said one or more capacitors to move said suspended platform to said desired height.

7. The detector according to claim 1, wherein the tuning of the coupling capacitance is realized through the control of the gap between an antenna sensor and said suspended platform.

8. The detector according to claim 1, wherein said sensor array is suspended by one or more holding arms which act as springs allowing said suspended platform to move.

9. The detector according to claim 1, wherein said sensor array is suspended by one or more holding arms which act as a spring allowing said suspended platform to move, wherein applying a DC bias to said capacitor plates generates an attractive force to move said suspended platform in the vertical direction, whereby the final position of said suspended platform is determined by a balance between an electro-static force and an opposite mechanical force exerted by said spring.

10. A terahertz (THz) detector assembly, comprising:
a first dielectric substrate;
an antenna array fabricated on said first substrate, said antenna array including a first capacitive plate;
a second dielectric substrate;
a sensor array constructed on said second dielectric substrate, said sensor array comprising a suspended platform including a second capacitive plate, a thermal sensor and an electrical load coupled to said second capacitive plate, said suspended platform suspended by one or more holding arms connected to said second dielectric substrate which act as springs allowing said suspended platform to move;
wherein a coupling capacitor is formed by vertically joining said antenna array to said sensor array such that said first capacitive plate and said second capacitance plate are separated by a gap; and
wherein said sensor array is operative to transfer THz energy received by said antenna array to said electrical load via said coupling capacitor and to convert the heat generated by said electrical load to an electrical signal, wherein said capacitive coupling provides thermal isolation between said antenna array and said sensor array.

11. The detector according to claim 10, wherein said coupling capacitor functions as an electro-static actuator upon the application of a DC bias voltage across said coupling capacitor.

12. The detector according to claim 10, wherein the tuning of said coupling capacitor is realized through the control of the gap formed between an antenna sensor and said suspended platform.

13. The detector according to claim 10, wherein applying a DC bias across said coupling capacitor generates an attractive force to move said suspended platform, whereby the final position of said suspended platform is determined by a balance between an electro-static force generated by said coupling capacitor and an opposite mechanical force exerted by said spring.

14. The detector according to claim 10, further comprising discharge means for fast discharging of the suspended platform's radiation induced heat by causing a touching of said suspended platform to said antenna array.

15. The detector according to claim 10, further comprising modulation means for applying amplitude modulation to an electro-optical signal through periodic variation of the coupling capacitor gap.

16. A terahertz (THz) detector assembly, the method comprising:
a first dielectric substrate;
an antenna fabricated on said first substrate, said antenna including a first capacitive plate;
a second dielectric substrate;
a suspended platform constructed from said second dielectric substrate and connected thereto via one or more holding arms which act as springs allowing said suspended platform to move, said suspended platform comprising a second capacitive plate, an electrical load and a thermal sensor;
wherein a coupling capacitor and associated gap are formed by vertically joining said antenna to said suspended platform sensor array, said coupling capacitor operative to transfer energy received by said antenna to said electrical load, said thermal sensor operative to convert the heat generated by said electrical load to an electrical signal; and
wherein said coupling capacitor also functions as an electro-static actuator upon application of a DC bias applied across it which generates an attractive force to move said suspended platform in the vertical direction, whereby the final position of said suspended platform is determined by a balance between the electro-static force and an opposite mechanical force exerted by said springs.

17. The detector according to claim 16, wherein said capacitive coupling provides thermal isolation between said antenna array and said sensor array.

18. The detector according to claim 16, wherein said vertically joining said antenna to said suspended platform sensor array forms a plurality of capacitors.

19. The detector according to claim 16, wherein said coupling capacitor is tuned by controlling the gap formed between an antenna sensor and said suspended platform.

20. The detector according to claim 16, further comprising discharge means for fast discharging of radiation induced heat from said suspended platform by activating said electro-static actuator to touch the suspended platform to said antenna array.

21. The detector according to claim 16, further comprising modulation means for applying amplitude modulation to the received signal through periodic variation of the coupling capacitor gap.

22. The detector according to claim 16, further comprising read-out means operative to perform a correlated double sampling algorithm for reducing low frequency flicker 1/f noise.

* * * * *